(12) United States Patent
Esch

(10) Patent No.: US 7,438,723 B2
(45) Date of Patent: Oct. 21, 2008

(54) LENS SYSTEM AND METHOD FOR POWER ADJUSTMENT USING EXTERNALLY ACTUATED MICROPUMPS

(75) Inventor: Victor Esch, Albuquerque, NM (US)

(73) Assignee: PowerVision, Inc., Belmont, CA (US)

( * ) Notice: Subject to any disclaimer, the term of this patent is extended or adjusted under 35 U.S.C. 154(b) by 1215 days.

(21) Appl. No.: 10/734,404

(22) Filed: Dec. 12, 2003

(65) Prior Publication Data
US 2004/0190153 A1    Sep. 30, 2004

Related U.S. Application Data

(63) Continuation-in-part of application No. 10/717,832, filed on Nov. 19, 2003, now Pat. No. 6,836,374.

(60) Provisional application No. 60/433,049, filed on Dec. 12, 2002.

(51) Int. Cl.
A61F 2/16 (2006.01)
G02B 1/06 (2006.01)
(52) U.S. Cl. .................... 623/6.13; 623/6.14; 359/665
(58) Field of Classification Search ....... 623/6.13–6.15, 623/6.11
See application file for complete search history.

(56) References Cited

U.S. PATENT DOCUMENTS

| | | |
|---|---|---|
| 4,253,199 A | 3/1981 | Banko |
| 4,373,218 A | 2/1983 | Schachar |
| 4,409,691 A | 10/1983 | Levy |
| 4,435,856 A | 3/1984 | L'Esperance |
| 4,490,860 A | 1/1985 | Rainin |
| 4,494,254 A | 1/1985 | Lopez |
| 4,512,040 A | 4/1985 | McClure |
| 4,575,373 A | 3/1986 | Johnson |
| 4,585,457 A | 4/1986 | Kalb |
| 4,615,701 A | 10/1986 | Woods |
| 4,685,921 A | 8/1987 | Peyman |
| 4,685,922 A | 8/1987 | Peyman |
| 4,693,717 A | 9/1987 | Michelson |
| 4,731,078 A | 3/1988 | Stoy et al. |
| 4,731,080 A | 3/1988 | Galin |
| 4,787,903 A | 11/1988 | Grendahl |
| 4,790,847 A | 12/1988 | Woods |

(Continued)

FOREIGN PATENT DOCUMENTS

| | | |
|---|---|---|
| JP | 9294754 | 11/1997 |
| JP | 11276509 | 10/1999 |
| WO | WO 97/06751 A | 2/1997 |
| WO | WO 00/41650 A1 | 7/2000 |
| WO | WO 01/97742 A2 | 12/2001 |
| WO | WO 2004/010895 A2 | 2/2004 |
| WO | WO 2004/046768 A2 | 6/2004 |
| WO | WO 2004/072689 A2 | 8/2004 |

OTHER PUBLICATIONS

Esch et al; U.S. Appl. #11/844,108 entitled "Accommodating Intraocular Lens System and Method" filed Aug. 23, 2007.

(Continued)

*Primary Examiner*—Suzette J Gherbi
(74) *Attorney, Agent, or Firm*—Shay Glenn LLP

(57) ABSTRACT

An intraocular lens is provided that having optical parameters that may be adjusted in-situ, and is particularly useful in cataract patients that require an adjustment in the optical power of the lens post-implantation. The lens body carries an array of interior fluid-filled cells in which fluid is controllably moved by micropumps upon application of energy from an external source to move a fluid media into the cells to thereby alter the lens surface shape.

27 Claims, 6 Drawing Sheets

U.S. PATENT DOCUMENTS

| | | | |
|---|---|---|---|
| 4,816,031 A | 3/1989 | Pfoff | |
| 4,836,201 A | 6/1989 | Patton et al. | |
| 4,842,601 A | 6/1989 | Smith | |
| 4,848,343 A | 7/1989 | Wallsten et al. | |
| 4,888,012 A | 12/1989 | Horn et al. | |
| 4,892,543 A | 1/1990 | Turely | |
| 4,902,293 A | 2/1990 | Feaster | |
| 4,932,966 A | 6/1990 | Christie et al. | |
| 4,946,469 A | 8/1990 | Sarafarazi | |
| 4,950,289 A | 8/1990 | Krasner | |
| 4,963,148 A | 10/1990 | Sulc et al. | |
| 4,994,082 A | 2/1991 | Richards et al. | |
| 4,995,879 A | 2/1991 | Dougherty | |
| 5,015,254 A | 5/1991 | Greite | |
| 5,035,710 A | 7/1991 | Nakada et al. | |
| 5,047,051 A | 9/1991 | Cumming | |
| 5,066,301 A | 11/1991 | Wiley | |
| 5,145,935 A | 9/1992 | Hayashi | |
| 5,152,789 A | 10/1992 | Willis | |
| 5,171,266 A | 12/1992 | Wiley et al. | |
| 5,201,763 A | 4/1993 | Brady et al. | |
| 5,213,579 A | 5/1993 | Yamada et al. | |
| 5,235,003 A | 8/1993 | Ward et al. | |
| 5,275,623 A | 1/1994 | Sarfarazi | |
| 5,275,624 A | 1/1994 | Hara et al. | |
| 5,288,293 A | 2/1994 | O'Donnell, Jr. | |
| 5,326,347 A | 7/1994 | Cumming | |
| 5,405,386 A | 4/1995 | Rheinish et al. | |
| 5,443,506 A | 8/1995 | Garabet | |
| 5,444,106 A | 8/1995 | Zhou et al. | |
| 5,476,514 A | 12/1995 | Cumming | |
| 5,489,302 A | 2/1996 | Skottun | |
| 5,496,366 A | 3/1996 | Cumming | |
| 5,506,300 A | 4/1996 | Ward et al. | |
| 5,578,081 A | 11/1996 | McDonald | |
| 5,593,436 A | 1/1997 | Langerman | |
| 5,607,472 A | 3/1997 | Thompson | |
| 5,628,795 A | 5/1997 | Langerman | |
| 5,665,822 A | 9/1997 | Bitler et al. | |
| 5,674,282 A | 10/1997 | Cumming | |
| 5,697,973 A | 12/1997 | Peyman et al. | |
| 5,702,441 A | 12/1997 | Zhou | |
| 5,774,273 A | 6/1998 | Bornhorst | |
| 5,843,188 A | 12/1998 | McDonald | |
| 5,891,931 A | 4/1999 | Leboeuf et al. | |
| 5,928,282 A | 7/1999 | Nigam | |
| 5,984,962 A | 11/1999 | Anello et al. | |
| 6,013,101 A | 1/2000 | Israel | |
| 6,015,842 A | 1/2000 | Leboeuf et al. | |
| 6,117,171 A | 9/2000 | Skottun | |
| 6,124,980 A | 9/2000 | Cerbell | |
| 6,139,576 A | 10/2000 | Doyle et al. | |
| 6,176,878 B1 | 1/2001 | Gwon et al. | |
| 6,188,526 B1 | 2/2001 | Sasaya et al. | |
| 6,190,410 B1 | 2/2001 | Lamielle et al. | |
| 6,195,807 B1 * | 3/2001 | Chou | 2/428 |
| 6,217,612 B1 | 4/2001 | Woods | |
| 6,225,367 B1 | 5/2001 | Chaouk et al. | |
| 6,299,641 B1 | 10/2001 | Woods | |
| 6,302,911 B1 | 10/2001 | Hanna | |
| 6,322,589 B1 | 11/2001 | Cumming | |
| 6,342,073 B1 | 1/2002 | Cumming et al. | |
| 6,387,126 B1 | 5/2002 | Cumming | |
| 6,388,043 B1 | 5/2002 | Langer et al. | |
| 6,406,494 B1 | 6/2002 | Laguette et al. | |
| 6,443,985 B1 | 9/2002 | Woods | |
| 6,450,642 B1 | 9/2002 | Jethmalani et al. | |
| 6,464,725 B2 | 10/2002 | Skotton | |
| 6,488,708 B2 | 12/2002 | Sarfarazi | |
| 6,493,151 B2 * | 12/2002 | Schachar | 359/666 |
| 6,503,276 B2 | 1/2003 | Lang et al. | |
| 6,551,354 B1 | 4/2003 | Ghazizadeh et al. | |
| 6,552,860 B1 * | 4/2003 | Alden | 359/742 |
| 6,554,859 B1 | 4/2003 | Lang et al. | |
| 6,592,621 B1 | 7/2003 | Domino | |
| 6,599,317 B1 | 7/2003 | Weinschenk, III et al. | |
| 6,610,350 B2 | 8/2003 | Suzuki et al. | |
| 6,616,692 B1 | 9/2003 | Glick et al. | |
| 6,638,305 B2 | 10/2003 | Laguette | |
| 6,638,306 B2 | 10/2003 | Cumming | |
| 6,645,245 B1 | 11/2003 | Preussner | |
| 6,645,246 B1 | 11/2003 | Weinschenk, III et al. | |
| 6,660,035 B1 | 12/2003 | Lang et al. | |
| 6,692,525 B2 | 2/2004 | Brady et al. | |
| 6,695,881 B2 | 2/2004 | Peng et al. | |
| 6,709,108 B2 | 3/2004 | Levine et al. | |
| 6,712,848 B1 | 3/2004 | Wolf et al. | |
| 6,730,123 B1 | 5/2004 | Klopotek | |
| 6,749,632 B2 | 6/2004 | Sandstedt et al. | |
| 6,827,738 B2 | 12/2004 | Willis et al. | |
| 6,836,374 B2 * | 12/2004 | Esch et al. | 359/665 |
| 6,860,601 B2 | 3/2005 | Shadduck | |
| 6,926,736 B2 | 8/2005 | Peng et al. | |
| 6,935,743 B2 | 8/2005 | Shadduck | |
| 6,966,649 B2 | 11/2005 | Shadduck | |
| 6,969,403 B2 | 11/2005 | Peng et al. | |
| 7,068,439 B2 | 6/2006 | Esch et al. | |
| 7,122,053 B2 | 10/2006 | Esch | |
| 7,217,288 B2 | 5/2007 | Esch et al. | |
| 7,264,351 B2 | 9/2007 | Shadduck | |
| 7,278,739 B2 | 10/2007 | Shadduck | |
| 2001/0001836 A1 | 5/2001 | Cumming | |
| 2001/0016771 A1 | 8/2001 | Cumming | |
| 2002/0055777 A1 | 5/2002 | Cumming et al. | |
| 2002/0072795 A1 | 6/2002 | Green | |
| 2002/0095212 A1 | 7/2002 | Boehm | |
| 2002/0107568 A1 | 8/2002 | Zadno-Azizi et al. | |
| 2002/0111678 A1 | 8/2002 | Zadno-Azizi et al. | |
| 2002/0116057 A1 | 8/2002 | Ting et al. | |
| 2002/0116058 A1 | 8/2002 | Zadno-Azizi et al. | |
| 2002/0116059 A1 | 8/2002 | Zadno-Azizi et al. | |
| 2002/0116060 A1 | 8/2002 | Nguyen et al. | |
| 2002/0116061 A1 | 8/2002 | Zadno-Azizi et al. | |
| 2002/0161434 A1 | 10/2002 | Laguette et al. | |
| 2002/0193876 A1 | 12/2002 | Lang et al. | |
| 2003/0003295 A1 | 1/2003 | Dreher et al. | |
| 2003/0018384 A1 | 1/2003 | Valyunin et al. | |
| 2003/0050695 A1 | 3/2003 | Lin et al. | |
| 2003/0050696 A1 | 3/2003 | Cumming | |
| 2003/0060878 A1 | 3/2003 | Shadduck | |
| 2003/0060881 A1 | 3/2003 | Glick et al. | |
| 2003/0078656 A1 | 4/2003 | Nguyen | |
| 2003/0078657 A1 | 4/2003 | Zadno-Aziz et al. | |
| 2003/0078658 A1 | 4/2003 | Zadno-Azizi | |
| 2003/0083744 A1 | 5/2003 | Khoury | |
| 2003/0109925 A1 | 6/2003 | Ghazizadeh et al. | |
| 2003/0109926 A1 | 6/2003 | Portney | |
| 2003/0130732 A1 | 7/2003 | Sarfarazi | |
| 2003/0135272 A1 | 7/2003 | Brady et al. | |
| 2003/0149480 A1 | 8/2003 | Shadduck | |
| 2003/0158599 A1 | 8/2003 | Brady et al. | |
| 2003/0171808 A1 | 9/2003 | Phillips | |
| 2003/0187505 A1 | 10/2003 | Liao | |
| 2003/0199977 A1 | 10/2003 | Cumming | |
| 2004/0001180 A1 * | 1/2004 | Epstein | 351/159 |
| 2004/0006386 A1 | 1/2004 | Valint et al. | |
| 2004/0006387 A1 | 1/2004 | Kelman | |
| 2004/0008419 A1 * | 1/2004 | Schachar | 359/666 |
| 2004/0015236 A1 | 1/2004 | Sarfarazi | |
| 2004/0039446 A1 | 2/2004 | McNicholas | |
| 2004/0054408 A1 | 3/2004 | Glick et al. | |
| 2004/0059343 A1 | 3/2004 | Shearer et al. | |
| 2004/0082994 A1 | 4/2004 | Woods et al. | |
| 2004/0085511 A1 | 5/2004 | Uno et al. | |

| | | |
|---|---|---|
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0181279 A1 | 9/2004 | Nun |
| 2004/0190153 A1 | 9/2004 | Esch |
| 2005/0021139 A1 | 1/2005 | Shadduck |
| 2005/0119740 A1 | 6/2005 | Esch et al. |
| 2005/0131535 A1 | 6/2005 | Woods |
| 2005/0149183 A1* | 7/2005 | Shadduck .................. 623/6.13 |
| 2005/0264756 A1 | 12/2005 | Esch |
| 2006/0041307 A1 | 2/2006 | Esch et al. |
| 2007/0010880 A1 | 1/2007 | Esch |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0203578 A1 | 8/2007 | Scholl et al. |
| 2007/0213817 A1 | 9/2007 | Esch et al. |
| 2007/0299487 A1 | 12/2007 | Shadduck |
| 2008/0015689 A1 | 1/2008 | Esch et al. |

OTHER PUBLICATIONS

Smith et al; U.S. Appl. #11/844,087 entitled "Accommodating Intraocular Lens System Having Spherical Aberration Compensation and Method," filed Aug. 23, 2007.

Wyant et al; "Basic Wavefront Aberration Theory for Optical Metrology," Applied Optics and Optical Engineering, vol. XI, 1992:1-13.

* cited by examiner

US 7,438,723 B2

LENS SYSTEM AND METHOD FOR POWER ADJUSTMENT USING EXTERNALLY ACTUATED MICROPUMPS

REFERENCE TO RELATED APPLICATIONS

This application claims the benefit of priority from U.S. provisional application 60/433,049, filed Dec. 12, 2002, and is a continuation-in-part of U.S. patent application Ser. No. 10/717,832, filed Nov. 19, 2003.

FIELD OF THE INVENTION

The present invention relates to intraocular lenses ("IOLs") having optical parameters that are adjustable in-situ. More particularly, the present invention relates to IOLs for in-capsule implantation for cataract patients wherein an external energy source is applied to the lens to actuate micropumps that control movement of fluid media within the interior of the lens, thereby altering the lens curvature to correct aberrations.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, the patient typically needs glasses for reading. The surgeon selects the power of the IOL based on analysis of refractive characteristics of the patient's eye prior to the surgery. However, in a significant number of cases, after the patient's eye has healed from the cataract surgery, there is a refractive error that could not be predicted. It is quite common for residual errors after IOL implantation to occur, and in fact, such errors may occur in the vast majority of IOL patients. This error reportedly averages approximately 0.6 diopters, with a +/−0.5 standard deviation. Thus, many patients experience an error of over 1.0 diopter.

Various types of methods and apparatus have been proposed for altering the corrective power of an ophthalmic lens in-situ. For example, U.S. Pat. No. 6,450,642 to Jethmalani et al. describes a lens that is capable of post-fabrication power adjustment. Specifically, a partially polymerized polymer lens matrix is described that is capable of stimulus-induced further polymerization to permanently alter the lens in a selected shape.

U.S. Pat. No. 5,443,506 to Garabet describes a fluid-filled lens wherein the focusing power may be altered by changing the index of refraction of fluid carried within a central optic portion. U.S. Pat. No. 5,066,301 to Wiley describes an IOL having a fluid-filled or gel-filled lens that carries a plurality of light-reflective particles, wherein the orientation of the particles is controlled by an electromagnetic field to thereby alter the spherical power of the lens. In another similar approach, U.S. Pat. No. 4,787,903 to Grendahl discloses a fresnel-type IOL with an overlying layer of a liquid crystalline composition that has a variable index of refraction depending upon its stimulation by electrical or light energy to provide a post-implant adjustability.

U.S. Pat. No. 4,816,031 to Pfoff discloses an IOL with a hard PMMA lens separated by a single chamber from a flexible thin lens layer. The lens assembly is adjusted by microfluid pumps that vary a volume of fluid between the PMMA lens portion and the thin layer portion. U.S. Pat. No. 5,288,293 to O'Donnell discloses an intraocular lens comprising a plurality of layers of materials that respond to the application of laser energy to form microfenestrations that alter the anterior lens curvature.

Although previously known workers in the field of in-situ adjustable lenses have made some progress, the relative complexity of the methods and apparatus developed to date have prevented widespread commercialization of such devices. Moreover, previously known methods and apparatus have been directed to in-situ modifications that attempt to alter the lens axial position within the eye or overall curvature of the lens. However, such gross modifications to lens position or curvature are limited by materials and space constraints.

In view of the foregoing, it would be desirable to develop in-situ adjustable intraocular lenses that overcome the drawbacks of previously known devices. It would therefore be desirable to provide apparatus and methods that enable localized modification of the surface of an intraocular lens to correct errors, such as defocus error. This may be commonly thought of as moving the focus of the IOL system to the retina, and may be effected by actual axial motion and/or modification of the surface of the IOL, e.g., by changing the radius of curvature of one or more of the surfaces of the IOL.

In addition to modifying the placement of the focal point at the retina, it would be desirable to provide methods and apparatus that permit in-situ localized correction of other aberration properties of the eye, for example astigmatism of the eye, which may be associated with the cornea, or to correct higher order aberrations to improve visual acuity.

It also would be advantageous to provide methods and apparatus for periodically manipulating the surface of an IOL on a localized basis after the IOL has been implanted and the access incision has healed. In order to provide such in-situ modification of the IOL surface, it would be desirable to provide an IOL configured to be modified, one either a one-time basis or periodically, by application of energy from a remote source, such as a laser, radio-frequency energy or ultrasonically.

SUMMARY OF THE INVENTION

In view of the foregoing, it is an object of the present invention to provide apparatus and methods that enable localized in-situ modification of the surface of an intraocular lens to correct errors, such as defocus error, astigmatism and higher order aberrations.

It is also an object of this invention to provide apparatus and methods that enable localized in-situ modification of the surface of a lens to not only restore loss of sight due to cataracts, but which actually improve visual acuity.

It is another object of the present invention to provide methods and apparatus for periodically manipulating the surface of an IOL on a localized basis after the IOL has been implanted and the access incision has healed.

It is a further object of the present invention to provide methods and apparatus for in-situ localized modification of the lens surface, on either a one-time or periodic basis, by application of energy from a remote source, such as a laser, radio-frequency energy, chemically or ultrasonically.

These and other objects of the present invention are accomplished by providing an intraocular lens including an optic element comprising resilient, locally-deformable anterior and posterior polymer elements sandwiched against an array of deformable cells. The array of deformable cells is index-matched to the anterior and posterior elements and may be surrounded by a fluid that also is index-matched with the polymer of the lens. Each of the deformable cells in turn defines a secondary fluid-filled chamber having an adjustable interior fluid volume coupled by an externally actuable micropump to a reservoir, so that changes in the volume of the deformable cells result in corresponding localized deformation of surfaces of the anterior and/or posterior elements.

The deformable cells generally are adapted to be moved controllably between a retracted position and an axially-extended position to engage and controllably deform the anterior and/or posterior lens element upon the application of energy from an external energy source, such as a laser source to the micropumps. The number of cells may vary from as few as one to more than 250, and may be controlled individually or in groups using the external power source. Because the micropumps of the present invention may be used repeatedly, an intraocular lens of the present invention may be periodically adjusted post-implant.

In accordance with the present invention, a selected number of deformable cells, or even a single cell, may be adjusted to alter a local region of the anterior and/or posterior lens surface, for example to correct an astigmatism or higher order aberration. Alternatively, the deformable cells within a region may be moved controllably to an axially extended position to alter the anterior and/or posterior lens surface globally to correct the sphere of the lens.

In accordance with one aspect of the present invention, an exemplary lens provides a micropump controlled fluid inflow channel and a relief valve controlled outflow channel that communicate with each fluid-filled cell. The micropumps are coupled between the inflow channel and a reservoir system disposed in a non-optic portion of the lens. Power adjustment of the lens therefore may be performed on a one-time basis or may be periodically repeated post-implant over the lifetime of the patient.

Methods of using and adjusting the lens of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to an in-situ adjustable intraocular lens system. In accordance with the principles of the present invention, methods and apparatus are provided wherein a lens has a locally deformable surface coupled to one or more fluid-filled actuators or cells controlled by externally actuable micropumps. The volume within, and deformation of, the fluid-filled cells is controlled by selective actuation, using an external power source, of micropumps and/or relief valves coupled between the cells and one or more reservoirs.

Subsequent to implantation of the IOL and healing of the access incision, the IOL would approximate the appropriate power for the individual eye; the optical path difference ("OPD") of the lens then may be adjusted to optimize the optical performance in-situ. As described herein below, the net effect of modifying each cell element, each and in concert, is to provide for the improvement of the optical performance of the optical system, for example the human eye, in which the lens element is placed. By the proper choice of the extent of displacement of the cell or actuator, either increasing the OPD or decreasing it, the IOL may be made to cancel all or a substantial portion of the optical imperfection associated imaging system. Thus, an incoming wavefront from the cornea will impinge upon the IOL, and the aberrated wavefront can be substantially compared to ideal spherical wavefront. The individual cells or actuators then can be modified to impart the appropriate OPD upon the wavefront such that at the wavefront is substantially perfect after transmission through the lens.

Figure 1A:
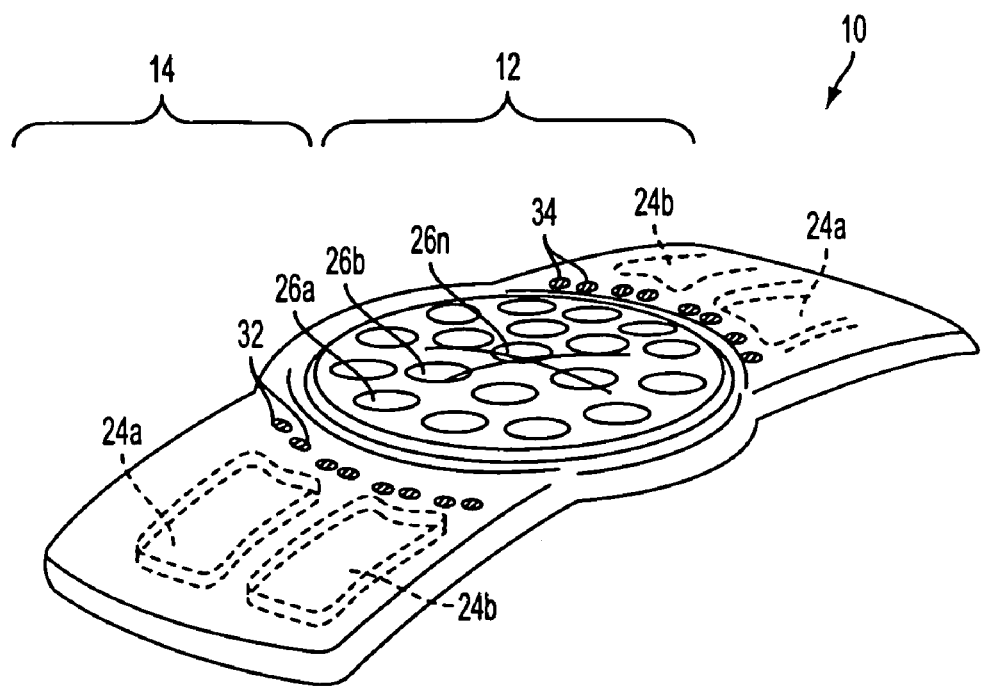
FIGS. 1A and 1B are, respectively, perspective and plan views of an exemplary embodiment of an intraocular lens of the present invention.
Figure 1B:
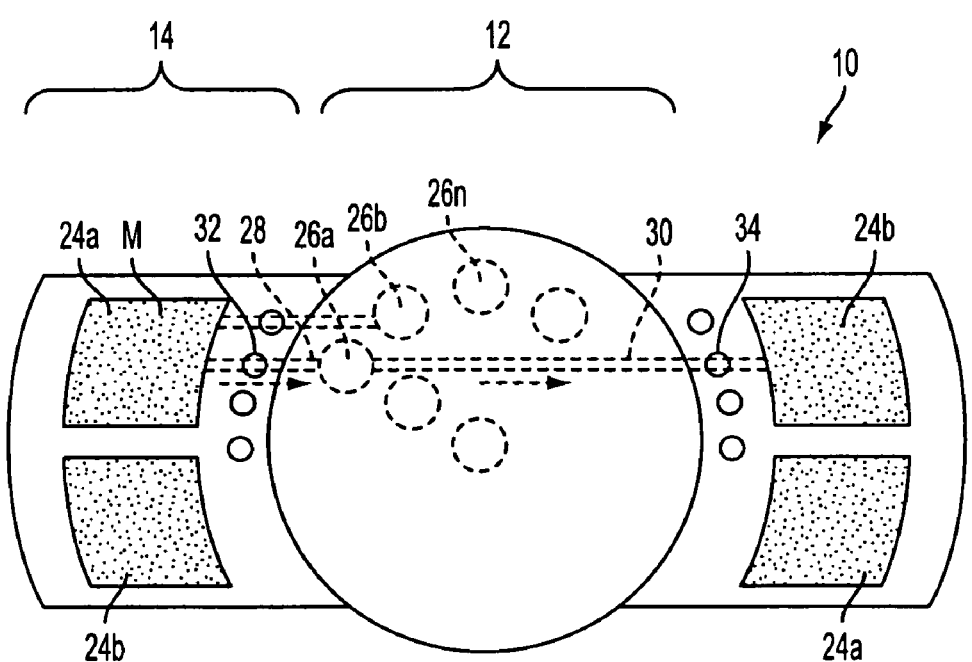
Figure 2:
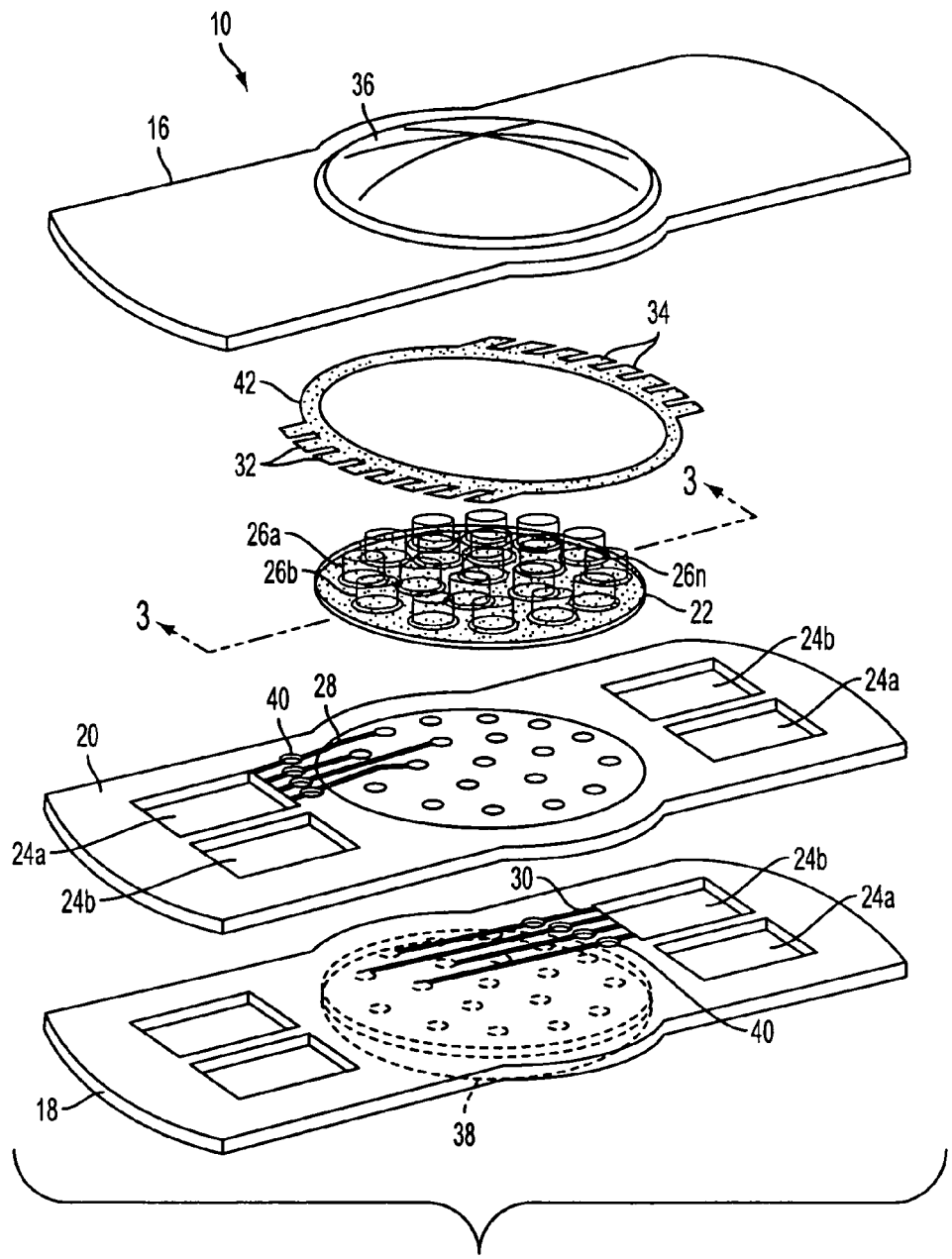
FIG. 2 is an exploded perspective of the intraocular lens of FIGS. 1A and 1B.

Referring to FIGS. 1A, 1B and 2, an exemplary embodiment of an intraocular lens constructed in accordance with the principles of present invention is described. Lens 10 includes optic portion 12 and non-optic or haptic portion 14 for engaging the lens capsule as when used in an in-the-capsule implant following cataract surgery. Non-optic portion 14 in the IOL of FIGS. 1 comprises a plate-type haptic but alternatively may comprise any type of arm-type haptics as known in the art. As is for conventional IOLs, the diameter of outermost portions of haptic portions 14 typically is about 13.0 mm while and the diameter of lens portion 10 is about 5.0 mm to 8.0 mm.

Optic portion 12 includes an array of deformable cells that are coupled to an anterior resilient polymer member, so that selective adjustment of an axial dimension of the deformable cells causes either localized or global adjustments to the optical parameters of optic portion 12. As described in further detail hereinbelow, adjustment of the axial dimension of the deformable cells preferably is accomplished in response to energy delivery from a remote source, for example from a laser source.

As shown in FIG. 2, lens 10 comprises anterior element 16 and posterior element 18 that are sandwiched against substrate 20. Substrate 20 carries array of deformable cells 22 and one or more reservoirs 24a, 24b, disposed in haptic portions 14. Each of elements 16, 18 20 and 22 are made of a transparent flexible, deformable material, such as silicone polymeric material, acrylic polymeric material, hydrogel polymeric material or the like, all of which allow the lens to be rolled or folded for carrying in the lumen of a small diameter introducer for subsequent deployment into the eye through a small incision. Preferably, the array of cells 22 and elements 16 and 18 are formed using injection-molding. Alternatively, elements 16 and 18 may be fabricated using turning or casting techniques known in the art. The choice of materials may be further informed by the requirements of mechanical properties, temperature sensitivity, optical properties such as dispersion, moldability properties, and so on.

Array of deformable cells 22 includes plurality of fluid-filled chambers or cells 26a, 26b . . . 26n. Illustratively, element 22 is shown having 19 such cells, although the actual number of cells may range between 1 and about 250. The interior of each cell 26a . . . 26n is coupled to fluid inflow channel 28 and outflow channel 30. Each inflow channel 28 includes micropump 32 coupled between the deformable cell and inflow reservoir 24a, and each outflow channel 30 includes relief valve 34. In a preferred embodiment, micropumps 32 and relief valves 34 are targetable and adapted for actuation by a laser source.

In accordance with the principles of the present invention, correction of defocus error and other aberrations may be addressed by the actuation and axial displacement of the surface of anterior or posterior elements at or about several localized paths. The deformable cell 26 underlying a targeted location of optic portion 12 may be altered in dimension by fluid flows to or from reservoirs 24a, 24b to increase or decrease the optical path along through the cell and the adjoining portions of the anterior and posterior elements 16 and 18. Each of several regions of optical portion 12 may be modified, either increasing or decreasing the optical path experienced by traversing the IOL at that location, as needed to correct the defocus error or other aberration.

In general, deformable cells 26 each actuate in a dimension substantially axial to the optical axis of the IOL, and may be addressed in groups or individually. Cells 26 are actuated through the addition of, or subtraction of, index-matched fluid media M from the cell. Movement of fluid M from reservoir 24a to a deformable cell is controlled by micropump 32, while movement of fluid away from a deformable cell to reservoir 24b is controlled by relief valve 34. In one embodiment, fluid is moved from higher pressure reservoir 24a to deformable-cells in discrete volumes by repeated actuation of micropumps 32, and may be relieved to lower pressure reservoirs 24b by continuous or intermittent activation of relief valves 34.

Fluid media M is selected so that it is index-matched to the material of deformable cells 26 and adjoining surfaces that might otherwise cause unwanted phase errors or diffractive effects. Silicones are examples of materials that are obtainable with equal index of refraction in both the liquid and solid state. Other materials may be chosen to match the index, using liquid silicones and solid PMMA, for example, or solid silicones and water solutions, or water. Thus the desired effect of index matching may be achieved so as to render the solid structure undetectable in the visible region of the spectrum.

Fluid manipulation and control may be through several methods appropriate to the external transmission of energy to the IOL to move fluid media M. As described above, lasers are expected to be particularly advantageous to provide usable power to actuate thermally-activated micropumps 32 and relief valves 34, described hereinbelow. In addition, other forms of micropumps and valves may be employed, including mechanisms that rely upon phase transition or swelling of materials, photo activation of polymers, and so on. The lens of the present invention also may employ photo-activated flow control mechanisms, whether thermo-mechanical, electro-mechanical, electromagnetic, fluid-magnetic, or any other appropriate type known in the art that may be activated externally. In this manner, aberrations of the eye then may be corrected by the appropriate addition or removal of fluid from individual cells as needed to provide the necessary correction.

As described more fully hereinbelow, the movement of fluid may be accomplished using micropumps and relief valves that mediate pressure differentials between the interiors of cells 26 and one or more reservoirs 24a, 24b of higher or lower pressure. For example, two reservoirs may be employed such that the relation $P_{fill} > P_{cell} > P_{empty}$ is maintained throughout the full dynamic range of the cells that is required to provide proper correction of the performance of the optical system, such as the human eye, wherein $P_{fill}$ is the pressure of the high pressure reservoir, e.g., 24a, $P_{cell}$ is the pressure within cells 26, and $P_{empty}$ is the pressure within the lower pressure reservoir, e.g., reservoir 24b.

In one preferred embodiment, reservoir 24a comprises a positive pressure supply reservoir relative to the pressure within fluid-filled cells 26a . . . 26n and reservoir 24b comprises a negative pressure reservoir or sink reservoir relative to the pressure within cells 26a . . . 26n. Fluid M is controlled to flow into cells 26a . . . 26n from reservoirs 24a through micropumps 32 and inflow channels 28 to alter the curvature of optic portion 12 of anterior element 22 of the lens. Fluid M also may be moved out of cells 26a . . . 26n to reservoir 24b through relief valves 34 and outflow channels 30 to reverse any curvature changed in the optic portion 12.

As noted above, the components of lens 10 preferably are fabricated from a somewhat flexible polymer such as silicone, hydrophobic or hydrophilic acrylic, hydrogel, collamer or other polymer with any suitable index of refraction, as is known in the art. The combination of components all are of similar materials with a similar index, and may be assembled to provide a typical bi-convex lens or a plano-convex or concavo-convex lens.

Figure 3:
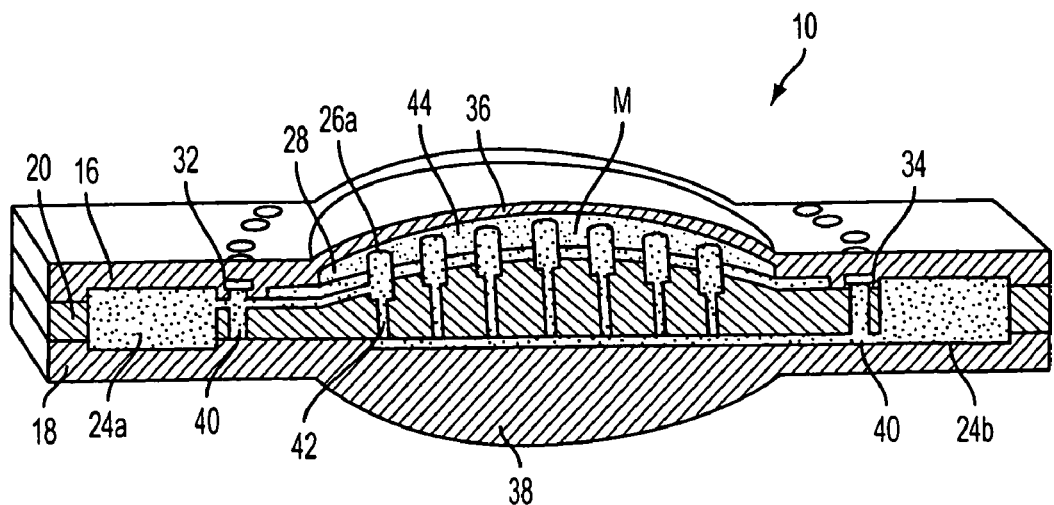
FIG. 3 is a side sectional view of the intraocular lens of FIGS. 1A and 1B.

Referring now also to FIG. 3, lens 10 has a bi-convex optic portion wherein anterior surface 36 has an anterior curvature and posterior surface 38. The exploded view of FIG. 2 illustrates that lens 10 is assembled from anterior element 16 and posterior element 18 together with substrate 20. Substrate 20 carries inflow channels 28 molded therein, while outflow channels 30 are shown as being molded into an interior surface of posterior element 18. It should be appreciated that the plurality of inflow and outflow channels may be molded into substrate 20 and/or any of the other interior surfaces of the anterior, substrate or posterior elements 16, 18 and 20. The interior of the lens body further includes array 22 of deformable cells 26a . . . 26n.

Inflow reservoir(s) 24a and outflow reservoir(s) 24b also are molded into the interior of the lens, with reservoir cavity portions extending into one or more of elements 16, 18 and 20. Substrate 20 also carries molded cavities 40 that are adapted to cooperate with photo-thermally responsive nickel titanium alloy micropump and relief valve component 42, described herein below. Cavities 40 alternatively may be molded into one of more of the anterior, posterior and substrate elements 16, 18 or 20.

It should be appreciated that the number of independent molded components of the lens may number from 2 to about 6, and that a variety of designs are possible for molding the plurality of cells 26a . . . 26n, inflow and outflow channels 28 and 30, reservoirs and cavities in the lens body, all of which fall within the scope of the invention.

Recent advances in microfluidics, so-called "soft" lithography and micro-molding make a lens of the type depicted in FIGS. 1-3 feasible with micron-scale features. Accordingly, it should be appreciated that the views of FIGS. 1-3 are provided to allow an understanding of the principles of operation of lens, are not-to-scale, and that the actual features of the inventive lenses may range in dimension from about 1 micron to 100 microns. For example, one company that has developed technology in die microfluidics fabrication field is Fluidigm Corporation, 7100 Shoreline Court, South San Francisco, Calif. 94080.

Fluidigm Corporation has developed technologies for forming and fabricating micron-scale channels, pumps, microvalves and other three-dimensional structures in multiple layers of soft polymers that function as fluidic circuitry. Multiple layers may be imprinted with the desired features and irreversibly bonded to one another by polymerization processes to provide a unitary lens body that has a uniform index of refraction. The fluid M that is provided within the fluidic circuitry of the lens may be a selected silicone fluid with a matching index of refraction.

A number of the technologies that enable the microfluidic elements of the present invention were developed at the California Institute of Technology in the 1990s. The following papers and materials are all incorporated herein by reference and describe fabrication techniques, components and aspects of microfluidics in soft polymers such as can be used to fabricate the lens of the present invention: S. R. Quake and A. Scherer, "From Micro to Nano Fabrication with Soft Materials", Science 290: 1536-40 (2000); P. Chou, M. A. Unger, and S. R. Quake, "A Microfabricated Rotary Pump", Biomedical Microdevices 3:323-330 (2001); M. A. Unger, H.-P. Chou, T. Thorsen, A. Scherer, and S. R. Quake, "Monolithic Microfabricated Valves and Pumps by Multilayer Soft Lithography", Science 288: 113-116 (2000); H. P. Chou, M. A. Unger, A. Scherer and S. R. Quake, "Integrated Elastomer Fluidic Lab on a Chip-Surface Patterning and DNA diagnostics", in Proceedings of the Solid State Actuator and Sensor Workshop, Hilton Head, S.C. (2000); H. P. Chou, C. Spence, A. Scherer and S. Quake, "A Microfabricated Device for Sizing and Sorting DNA Molecules", Proc. Nat'l Acad. Sci. 96: 11-13 (1999); A. Y. Fu, H. P. Chou, C. Spence, F. H. Arnold and S. R. Quake, "An Integrated Microfabricated Cell Sorter, Anal. Chem. (2002); and T. Thorsen, R. W. Roberts, F. H. Arnold and S. R. Quake, "Dynamic Pattern Formation in a Vesicle-Generating Microfluidic Device", Phys. Rev. Lett, 86: 4163-6 (2001).

Referring still to FIG. 3, a sectional array of deformable cells 22 is shown, where the section passes through several cells (e.g., 26a . . . 26n) that alter the anterior curvature of the lens. In this embodiment, positive pressure reservoir 24a is coupled by inflow channel 28 to the interior of cell 26a. Inflow channel 28 is formed in an upper surface of substrate 20 that extends from reservoir 24a through inflow cavity 40 and terminates at the base of fluid-filled cell 26a. Outflow channel 30 is defined in part by bore 42 through substrate 20 and further extends along an upper surface of posterior element 18 (and outflow cavity 40) to the negative pressure reservoir 24b. The lens assembly further defines space 44 about the exterior of the array of cells 22 and the interior of optic portion 12 of anterior element 16. Space 44 is filled with index-matched fluid M.

Figure 4A:
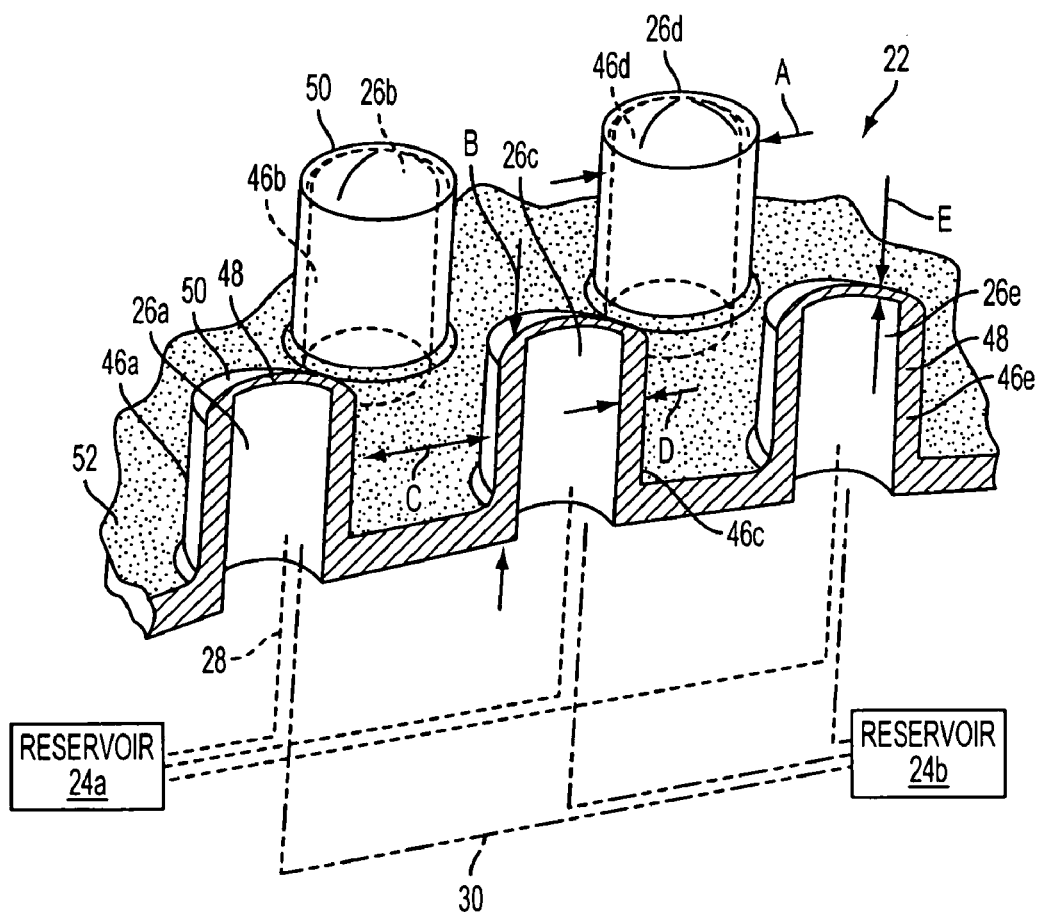
FIGS. 4A and 4B are detailed partial sectional perspective views of the deformable cells of the lens of FIGS. 1-3 depicting selective actuation of the deformable cells.
Figure 4B:
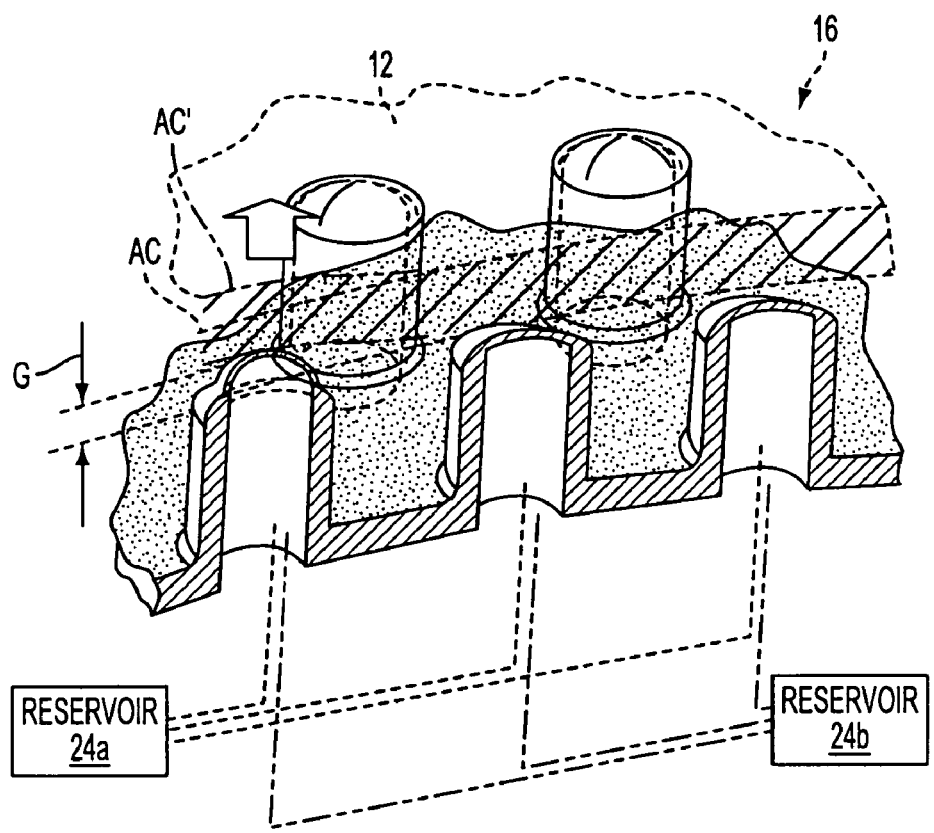

Turning now to FIGS. 4A and 4B, an enlarged view of a portion of array of cells 22 is provided to illustrate its method of use as well a methods of fabricating the component. Array 22 carries a plurality of cells 26a, 26b, 26c, 26d and 26e within molded structures 46a-46e. In general, as described above, the number of molded structures may range from 1 to about 200, and preferably is from about 20 to 120. Molded structures 46a . . . 46e extend generally orthogonal to the plane of substrate 20 (see FIG. 3) and are aligned with the optical axis of lens 10. Each molded structure 46a . . . 46e defines an exterior wall portion 48 and a substantially elastic deformable anterior wall portion indicated at 50 for engaging, deforming and adjusting the anterior lens surface. The base portion 52 of array 22 is adapted for bonding to an anterior surface of substrate 20.

Molded structures 46a . . . 46e and cells 26a . . . 26e therein may have any suitable dimensions and spacing therebetween. For example, dimension A represents a diameter of an exemplary structure 46d that may range between about 20 microns and 5 mm. The height of the structure 26c indicated at dimension B ranges between about 10 microns and 100 microns. The spacing C between the structures 26a and 26b may range between about 0 microns and 1000 microns. The thickness D of the exterior side walls 48 of the molded structures may range between about 10 microns and 200 microns.

The molded structures may vary in dimension, and in one embodiment the more centrally located structures may be larger or more spaced apart than the more peripheral molded structures. The molded structures may have any shape such as cylindrical, tapered, conical, hexagonal, etc. In a typical embodiment, the exterior wall portion 48 of each molded structure has a substantial thickness to prevent radial expansion of the structure and the cell therein when the volume of fluid M therein is increased in volume.

As may be seen by comparing FIGS. 4A and 4B, an inflow of fluid into the cell 26a expands the thin-wall anterior portion 50 a selected dimension indicated at G. This expansion of thin anterior wall 50 that bounds cell 26a engages and pushes anteriorly the resilient optic portion 12 of anterior element 16. Anterior wall 50 of molded structure 46a . . . 46e may range in thickness E from about 1 micron to 40 microns, and more preferably from about 2 microns to 20 microns. The amplitude G of movement of anterior wall 50 of each structure 46a . . . 46e may range from about 1 micron to 100 microns or more.

Expansion of cell 26a deforms and alters the anterior curvature AC of the lens to AC'. As will be understood from FIGS. 4A and 4B, lens 10 of the present invention provides for the correction of defocus error as well as other aberrations by the activation and axial displacement optic portion 12 of anterior element 16 of the lens at or about several localized paths. The cells 26a . . . 26n underlying the targeted locations are altered in dimension by fluid flows, wherein the effect is to increase or decrease the optical path of light through the altered portion of the lens.

In accordance with the principles of the present invention, each of several areas of the optic portion of the lens may be modified, either increasing or decreasing the optical path traversing the IOL in the altered lens portion. The optical aperture or lens surface thus may be separated into multiple individually addressable regions, with each molded structure capable of altering the anterior curvature AC in a dimension substantially axial to the optic axis of the IOL. Each element may be actuated through the addition of, or subtraction of, fluid media M from the dimensionally-alterable cells 26a . . . 26n.

It is important that the individual molded structures 46 and the corresponding cells act in unison so that no discontinuities exist between adjacent cells. The system of spaced apart deformable molded structures allows the system to create substantially smooth radii of curvature in the anterior lens surface, which is a function of, and controlled by, the cross-section A of the molded structures 46 and cells 26a . . . 26n, the spaced apart dimension C between the molded structures and the thickness, durometer and other physical properties of optic portion 12 of anterior element 16.

Space 44 between molded structures 46 and the interior surface of optic portion 12 of anterior element 16 contains the same index-matched fluid as is used in the fluid circuitry of the lens. Fluid M is selected such that it is index-matched to molded structures 46 of and adjoining surfaces that might otherwise cause unwanted phase errors or diffractive effects.

Figure 5:
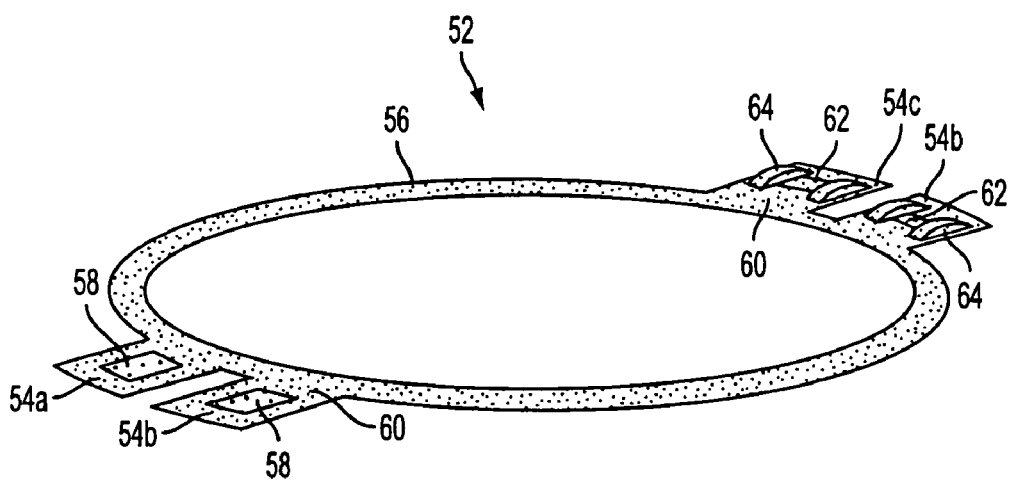
FIG. 5 is a perspective view of a thin-film nickel titanium alloy member, similar to that of FIG. 2 (de-mated from the lens body) illustrating a photo-thermally responsive shape memory alloy components of an exemplary micropump and relief valve.

Referring now to FIG. 5, an exemplary system and methods are described for controlling the flow of fluid into and out of the cells 26a . . . 26n and reservoirs 24a and 24b. Various types of micropumps and microvalves have been developed that are responsive to application of energy from a remote source, any one of which may be used in the lens according to the invention. The exemplary systems described herein are based on thin-film shape memory alloy (SMA) materials that actuate a diaphragm in response to a photothermal effect. Thus, the lens can be easily adapted to cooperate with a low power laser, galvanometric scanning system, and optional laser tracking system, all known on the art of laser refractive technologies, to target and actuate one or more mechanisms carried in lens 10.

Referring also to FIGS. 2 and 3, the intermediate region of lens 10 carries an annular member 52 of a thin-film nickel titanium (Nitinol) shape memory alloy. In general, the use of thin-film fabrication methods allow a single component to provide the diaphragm portions of the plurality of inflow and outflow micropump and relief valves that enable the operation of the lens.

As is well known, a nickel titanium alloy may be annealed so that it crystallizes in a manner that exhibits shape memory properties, a property that has found use in a number of medical implants such as endovascular stents. Virtually all uses of nickel titanium alloys have been developed from bulk materials in sheet or tubular forms. While various methods have been developed to draw tubes or to roll sheets of SMAs, conventional methods may be used to fabricate thin films in the 2 to 20 micron range needed for the invention.

Recently, techniques have been developed for sputter-deposited materials to provide thin film SMA materials, as well as to allow fabrication of MEMS components. Sputter-deposited thin film SMAs alloys such as nickel titanium films can be fabricated in a range of thickness from less than 1 micron to about 25 microns. The following papers describe methods of sputter-depositing thin films and annealing the SMA materials, which are incorporated herein by reference: V. Gupta, A. D. Johnson, V. Martynov, V. Galhotra, Thin Film Shape Memory Alloy for Medical Applications, NanoSpace 2000, an international micro/nano technology conference, Houston, Tex. Jan. 23-28, 2000; P. Krulevitch, A. P. Lee, P. B. Ramsey, J. C. Trevino, J. Hamilton, M. A. Northrup, Thin film Shape Memory Alloy Microactuators, J. Micromech. Microeng. Vol. 5, No. Dec. 4, 1996; A. David Johnson and Erik J. Shahoian, "Recent Progress in Thin Film Shape Memory Microactuators," MEMS '95, Proceedings IEEE Micro Electro Mechanical Systems, p. 216 (1995); S. Z Hua, C. M. Su, M. Wuttig, "Transformation Induced Stress in SMA Thin Films", MRS Symp. Proc. on Thin Films Stress and Mechanical Properties, 308, 525 (1993), and A. D. Johnson, Vacuum-Deposited TiNi Shape memory Film: Characterization and Applications in Micro-Devices, J. Micromech. Microeng. Vol.1, (1991) 34-41.

For use as a micropump or relief valve, the SMA material is annealed into a crystalline state wherein it undergoes a crystalline phase transformation from martensite to austenite when heated through the material's phase change transformation temperature. When below that temperature the material can be plastically deformed from a "memory shape" responsive to stress. When the SMA material is heated through the transformation temperature, it forcefully reverts to its memory shape, at the same time exerting considerable force.

In one lens embodiment, each cell, such as chamber 26a in FIG. 4B has associated micropump 32 and relief valve 34 for controlling inflows and outflows of fluid, respectively. It is desirable to limit the number of component parts and for this reason a micro-machined nickel titanium alloy mechanism may be best suited for the inventive lens. For convenience, the annular SMA member in FIG. 5 shows only four not-to-scale diaphragm portions 54a, 54b, 54c and 54d that extend away from annular portion 56. It will be appreciated that the number of diaphragm portions may be increased to any number needed for the invention.

Micropump diaphragm portions 54a and 54b define non-planar forms 58 that extend away from planar edges portions 60 of planar annular portion 56. Relief valve diaphragm portions 54c and 54d that define non-planar forms 62 that extend away from planar edges portions 60 and planar annular portion 56. Each non-planar form 62 is shown with an optional spring element 64 formed therein to assist in urging the relief valve to a closed position. The center of non-planar forms 58 and 62 also optionally may be coated with a light-absorbing composition that cooperates with a selected wavelength of light.

Figure 6A:
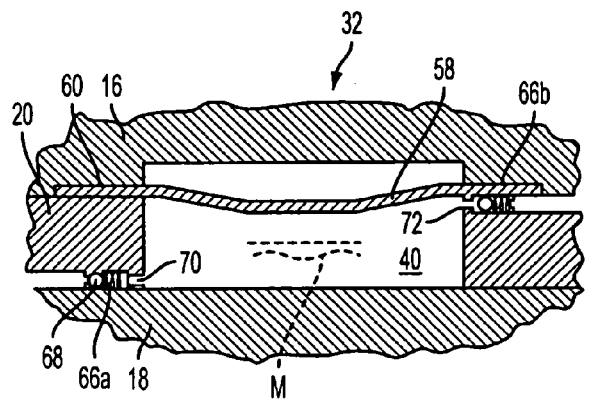
FIGS. 6A and 6B are, respectively, schematic sectional views of the thin-film nickel titanium micropump portion of the component of FIG. 5, after insert molding into the lens body, showing the initial and actuate positions of the micropump.
Figure 6B:
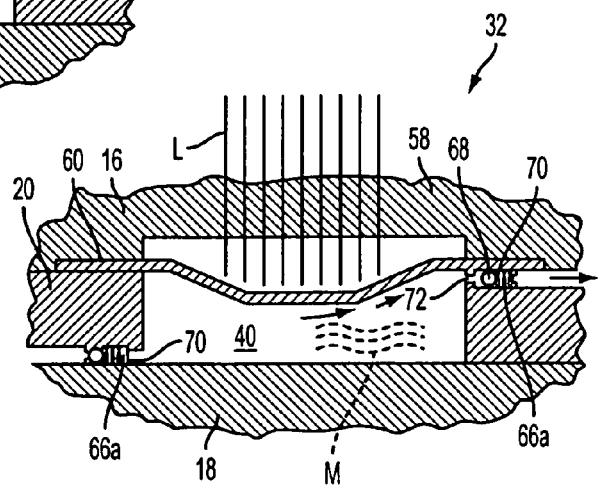

Referring now to FIGS. 6A and 6B, the operation of thermo-responsive micropump 32 is described. FIG. 6A is a sectional view of micropump 32 showing that planar edge portions 60 are sandwiched between a posterior surface of anterior element 16 and anterior surface of substrate 20, with diaphragm portion 58 disposed within cavity 40 the substrate. Each micropump 32 has two one-way valves 66a, 66b associated with it, located in inflow channel 28 on either side of cavity 40. One-way valves 66a and 66b illustratively are depicted as spring-biased ball valves, although other suitable one-way valves, such as flap valves or duck-bill valves, may be used. Each ball valve 66a, 66b includes ball 68 and spring 70 that biases the ball against seat 72. As is conventional, the ball may be unseated from the seat against the bias of the spring to permit fluid to flow through the valve in one direction, but closes against the seat to prevent flow in the opposite direction.

Micropump 32 is shown at rest in FIG. 6A, with diaphragm 58 in an initial position in which non-planar SMA portion 58 is contracted near the posterior surface of anterior element 16. One-way valves 66a, 66b are closed, and the space in cavity 40 beneath the non-planar SMA portion 58 is filled with fluid media M.

FIG. 6B shows micropump actuated by the photo-thermal targeting. Laser beam L is directed to impinge on the non-planar form 58 of the micropump. The increase in temperature of the non-planar form 58 causes the SMA to alter its dimension across the thin film expanse and bulge downward into cavity 40, thereby forcing the downstream one-way valve 66b to open and expelling fluid to a corresponding deformable cell, as indicated by the arrows in FIG. 6B. After fluid M is expelled through valve 66b, the valve recloses. When laser L is discontinued, non-planar SMA portion 58 cools, and contracts to the initial position shown in FIG. 6A. This creates a low pressure region in cavity 40, that causes valve 66a to open and recharge the space with fluid. As will be appreciated, micropump 32 could be repeatedly pulsed with laser L to add discrete volumes of fluid M to the interior of the corresponding deformable cell.

Figure 7A:
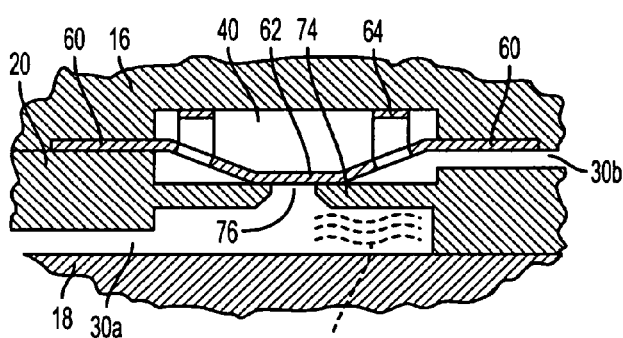
FIGS. 7A and 7B are, respectively, schematic sectional views of the thin-film nickel titanium alloy valve portion of the component of FIG. 5, after insert molding into the lens body, showing the normally closed and open positions of the relief valve.
Figure 7B:
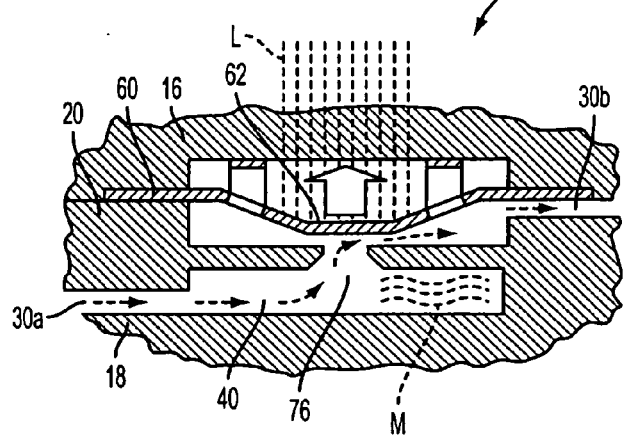

Referring now to FIGS. 7A and 7B, operation of thermo-responsive relief valve 34 is described. Relief valve 34 permits fluid to be drained through outflow channel 30 (see FIG. 1B) from a corresponding deformable cell to reservoir 24b. Relief valve 34 permits fine modulation of the alteration of optic portion 12, and also may be used to reduce deformation, e.g., if the patient's eye changes over time.

In FIG. 7A, relief valve 34 is shown with planar edge portions 60 sandwiched between the posterior surface of anterior element 16 and the anterior surface of substrate 20. Non-planar SMA portion 62 is disposed in cavity 40 of substrate 20. Relief valve 34 is shown at rest in a normally closed position with the non-planar SMA portion 62 pressed against valve seat 74 and closing off aperture 76. Outflow channel 30 has first portion 30a entering cavity 40 and second portion 30b exiting the cavity on the opposite side of closed-off aperture 76.

FIG. 7B shows relief valve 34 moved to an open position by the photo-thermal targeting. Laser beam L is directed to impinge on the non-planar form 62 of the valve. The increase in temperature of the non-planar form 62 causes the SMA to alter its dimension across the thin film expanse and lift away from the valve seat 76 to thereby open the valve. As indicated by the arrows, fluid then flows from a corresponding deformable cell to the sink reservoir.

The net effect of modifying fluid volume in cells 26a . . . 26n, each and in concert, is to improve the optical performance of the lens system. By the proper choice of the extent of displacement of cells 26a . . . 26n, either increasing the OPD or decreasing it, the IOL may be made to cancel all or a substantial portion of the optical imperfection associated imaging system. Thus, an incoming wavefront from the cornea will impinge upon the IOL, and the aberrated wavefront can be substantially compared to ideal spherical wavefront. The individual cells then may be modified to impart the appropriate OPD upon the wavefront such that the wavefront provides substantially improved vision correction for light transmitted through the lens.

The lens of the present invention, when used as an intraocular implant, may be coupled with a diagnostic instrument such as a Shack Hartman wavefront sensing system or any other type of wavefront sensor to provide real-time intraoperative feedback of the adjusted optical parameters of the lens. By this means, the lens may be optimized to correct both spherically and for higher order aberrations.

Figure 8:
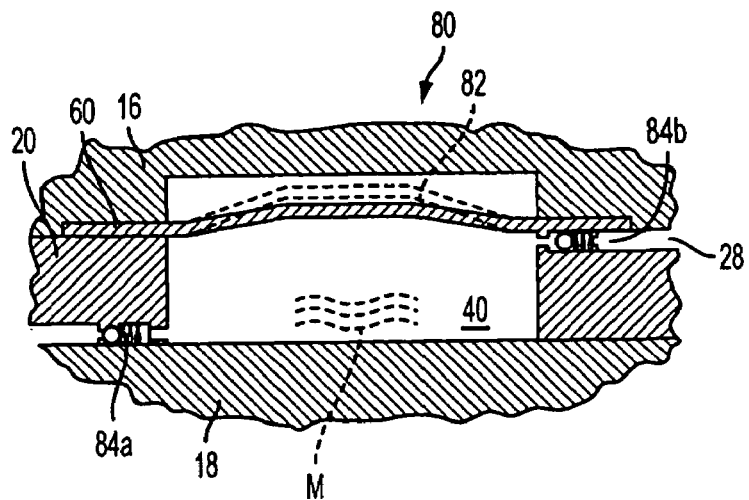
FIG. 8 is a schematic sectional view of and alternative micropump portion of the component of FIG. 5, after insert molding into the lens body.

Referring now to FIG. 8, an alternative embodiment of a thermo-responsive micropump of the present invention is described. Micropump 80 is similar in construction to micropump 32 of FIGS. 6A and 6B, except that non-planar SMA form 82 is concave upward rather than downward as in the embodiment of FIGS. 6. As for the previous embodiment, planar edge portions 60 are sandwiched between a posterior surface of anterior element 16 and anterior surface of substrate 20, with non-planar SMA form 82 disposed within cavity 40 the substrate. Micropump 80 includes one-way valves 84a, 84b, illustratively spring-biased ball valves, located in inflow channel 28 on either side of cavity 40.

Operation of micropump 80 is similar to that of micropump 32, and is shown in FIG. 8, with diaphragm 82 in its actuated position (i.e., as heated by a laser beam L, not shown). When so actuated, diaphragm 82 deflects downward into the cavity, expelling fluid through valve 84b. After the fluid is expelled through valve 84b, the valve recloses. When laser L is discontinued and non-planar SMA portion 82 cools, it contracts to its initial position disposed nearer to the posterior surface of anterior element 16 (shown in dotted line in FIG. 8). This movement causes valve 84a to open and recharge the space with fluid.

Figure 9:
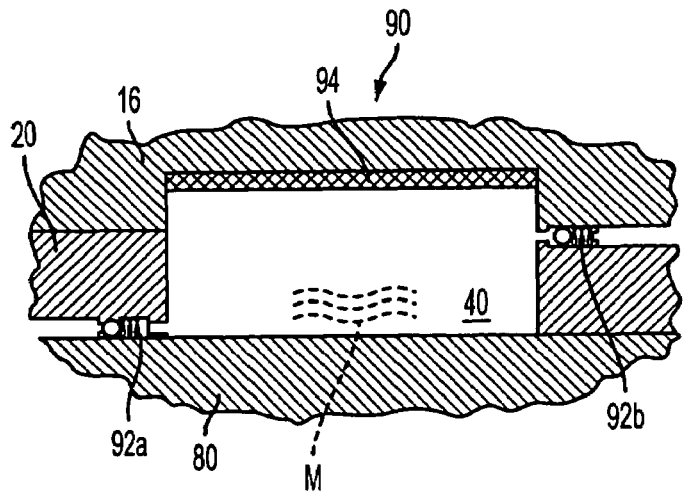
FIG. 9 is a schematic sectional view of another alternative micropump after insert molding into the lens body.

Turning to FIG. 9, another alternative embodiment of a thermo-responsive micropump of the present invention is described. Unlike micropumps 32 and 80, micropump 90 has no moving parts other than one-way valves 92a and 92b. Instead, micropump 90 includes absorptive layer 94 that is specifically selected to heat up when irradiated with a laser. One-way valves 92a, 94b again are illustratively spring-biased ball valves, located in inflow channel 28 on either side of cavity 40 in substrate 20.

In operation, a laser is targeted onto absorptive layer 94, which in turn heats the fluid within cavity 40 and causing it to expand. This increases the pressure within the micropump, driving the fluid through one-way valve 28 and into the interior of the corresponding deformable cell. When the laser is discontinued, valve 92b closes. As the fluid in cavity 40 cools further, it causes valve 92a to open and recharge the cavity. Preferably, absorptive layer 94 comprises a thin black anodized metallic element that enhances deposition of laser energy, and also may serve to prevent irradiation from the laser from passing beyond the IOL.

Alternatively, heating of fluid M in cavity 40 may be caused through the absorption of laser energy within the fluid itself, in which case the wavelength of the laser and the absorption of the material must be selected such that sufficient power is deposited for the desired expansion. In this case the wavelength of the laser must be selected consistent with benign transmission through the intervening materials of the eye, and with the requirement of laser safety with respect to retinal exposure.

Figure 10:
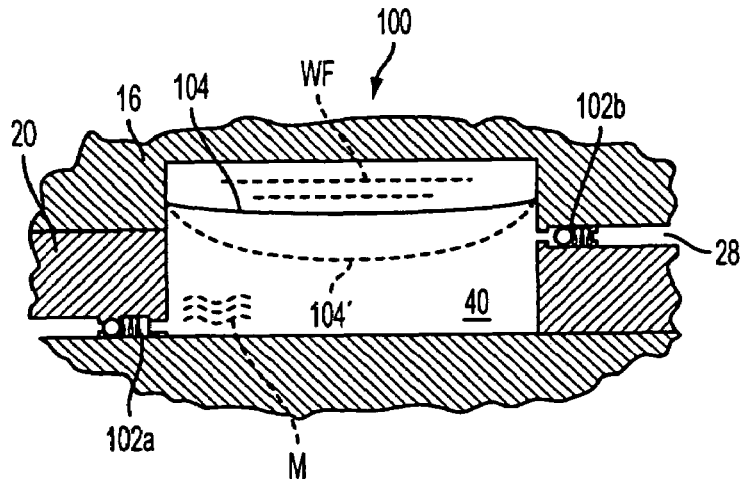
FIG. 10 is a schematic sectional view of a further exemplary micropump portion of the present invention after insert molding into the lens body.

Referring now to FIG. 10, an additional embodiment of a micropump suitable for use in the lens of the present invention is described. Micropump 100 comprises one-way valves 102a, 102b, expandable membrane 104 and working fluid WF. Working fluid WF preferably has high absorptivity at the irradiating wavelength, is nominally transmitted by the other lens materials, and has a much lower boiling point than fluid M contained in cavity 40. Accordingly, when irradiated by a laser, working fluid WF changes phase to a vapor, and drives expandable membrane 104 to position 104' (shown in dotted line). This in turn expels fluid from cavity 40 through valve 102b and into the interior of the deformable cell. When the laser is discontinued, valve 102b closes. As working fluid WF cools, it causes valve 102a to open and recharge the cavity.

As will be appreciated, to provide for the appropriate supply and management of fluids, and to provide for the movement of fluid into optic portion 12, multiple reservoirs high and low pressure reservoirs may be employed, as in the embodiment of FIGS. 1-3. In addition, if it were desirable to recycle fluid between the high and low pressure reservoirs, additional micropumps may be used, for example, to couple reservoirs 24a and 24b. In this case, if it were necessary to replenish higher pressure reservoir 24a, the micropump could be repeatedly actuated to transfer fluid from the low pressure reservoir to the high pressure reservoir, operating as described hereinabove.

Although the lens embodiment of FIGS. 1-3 provides a micropump for each inflow channel 28 and a relief valve for each outflow channel 30, it will be appreciated that the discrete number of micropumps and relief valves in a lens may be reduced in number by using a manifold that is coupled to each fluid-filled cell by a single inflow or outflow channel, wherein the manifold may be switched between being fluidly coupled to either a positive pressure or negative pressure pump or reservoir.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. An intraocular lens comprising:
a lens portion defining an anterior surface layer and a posterior surface layer;
an interior of the lens portion comprising an array of deformable cells each defining a volume of a selected fluid therein, each deformable cell in substantial engagement with either the anterior or posterior surface layer;
a micropump configured to control fluid flow to alter the volume in at least a portion of the array of deformable cells to deform the anterior or posterior surface layer and alter an optical parameter of the lens.

2. The intraocular lens of claim 1 wherein the array of deformable cells defines an axis that is substantially perpendicular to the anterior or posterior surface layer.

3. The intraocular lens of claim 1 wherein the array of deformable cells comprises round cells.

4. The intraocular lens of claim 1 further a reservoir communicating with each deformable cell via an inflow channel, the micropump interposed in the inflow channel between the deformable cell and the reservoir.

5. The intraocular lens of claim 4 wherein the micropump is photo-activated.

6. The intraocular lens of claim 4 wherein a single reservoir communicates with a subset of the array of deformable cells.

7. The intraocular lens of claim 4 wherein the reservoir is located within a periphery of the intraocular lens.

8. The intraocular lens of claim 1 further comprising a reservoir communicating with each deformable cell via an outflow channel and a relief valve interposed in the outflow channel between the deformable cell and the reservoir.

9. The intraocular lens of claim 8 wherein the relief valve is photo-activated.

10. The intraocular lens of claim 1 wherein the micropump comprises a bistable nickel-titanium alloy.

11. A power adjustable intraocular lens comprising:
a resilient lens body defining an anterior curvature and a posterior curvature;
an interior portion of the lens body including an array of deformable fluid-filled structures that engage a surface element of the lens body;
a micropump configured to control fluid flow into or out of at least one fluid-filled structure to thereby controllably deform and alter an optical parameter of the lens.

12. The intraocular lens of claim 11 further comprising:
a first reservoir in communication with an interior chamber of at least one fluid-filled structure via a first channel;
wherein the micropump is interposed in the first channel to control fluid flows to the interior chamber of the at least one fluid-filled structure.

13. The intraocular lens of claim 12 further comprising:
a second reservoir in communication with the interior chamber of at least one fluid-filled structure via a second channel; and
a relief valve interposed in the second channel to controlling fluid flows from the interior chamber of the at least one fluid-filled structure.

14. The intraocular lens of claim 13 wherein the first reservoir defines a high internal fluid pressure relative to each fluid-filled structure and the second reservoir defines a low internal fluid pressure relative to each fluid-filled structure.

15. The intraocular lens of claim 12 wherein the micropump is photo-thermally actuated.

16. The intraocular lens of claim 13 wherein the relief valve system is normally closed and is openable by application of energy from an external source.

17. The intraocular lens of claim 16 wherein the relief valve is photo-thermally actuated.

18. The intraocular lens of claim 11 wherein the micropump is actuable by application of energy from an external source.

19. The intraocular lens of claim 11 wherein the body of the fluid-filled structures and the fluid have matching indices of refraction.

20. The intraocular lens of claim 11 wherein the fluid-filled structures define a deformable engagement portion that engages a deformable surface element of the intraocular lens.

21. The intraocular lens of claim 11 wherein the array of deformable fluid-filled structures range in number between 1 and 500.

22. The intraocular lens of claim 11 wherein each one of the array of deformable fluid-filled structures has a cross section ranging between about 20 microns and 5 mm.

23. The intraocular lens of claim 11 wherein the array of deformable fluid-filled structures define a dynamic range between a retracted position and an extended position of between about 1 microns and 100 microns.

24. A method of adjusting the power of an intraocular lens comprising:
providing an intraocular lens body with a plurality of deformable fluid-filled structures in an interior of the intraocular lens that engage a surface element of the intraocular lens body; and
controllably altering the volume of the fluid within selected fluid-filled structures by selectively actuating a micropump to deform at least one of the fluid-filled structures and the surface element, thereby altering an optical parameter of the intraocular lens.

25. The method of claim 24 further comprising providing an index-matched fluid in a space in the intraocular lens body between an interior of the surface element and an exterior of the deformable fluid-filled structures.

26. The method of claim 24 wherein actuating a micropump comprises actuating a micropump with light energy from an external source.

27. The method of claim 24, further comprising actuating at least one relief valve from a normally closed position to an open position with light energy from an external source.

* * * * *